(12) United States Patent
Tsai et al.

(10) Patent No.: US 6,225,388 B1
(45) Date of Patent: May 1, 2001

(54) BIODEGRADABLE THERMOPLASTIC COMPOSITION WITH IMPROVED WETTABILITY

(75) Inventors: Fu-Jya Tsai; Brigitte C. Wertheim, both of Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/144,153

(22) Filed: Aug. 31, 1998

(51) Int. Cl.$^7$ ............................... C08K 5/20; C08K 5/09; C08K 5/13

(52) U.S. Cl. .................... 524/210; 524/321; 524/339; 524/378; 428/401

(58) Field of Search ..................... 524/210, 321, 524/339, 378; 428/401

(56) References Cited

U.S. PATENT DOCUMENTS

| | | | |
|---|---|---|---|
| 4,477,617 | * 10/1984 | Murphy | 524/136 |
| 4,710,187 | 12/1987 | Boland et al. | 604/385 A |
| 4,762,521 | 8/1988 | Roessler et al. | 604/38 SA |
| 4,770,656 | 9/1988 | Proxmire et al. | 604/393 |
| 4,798,603 | 1/1989 | Meyer et al. | 604/378 |
| 5,753,782 | * 5/1998 | Hammond et al. | 525/450 |

FOREIGN PATENT DOCUMENTS 0 569 153 A2  11/1993 (EP) ............... C08K/3/00

OTHER PUBLICATIONS

American Society for Testing Materials (ASTM) Designation: D 1238–E, "Standard Test Method for Flow Rates of Thermoplastics by Extrusion Plastometer," pp. 273–281, published Jan. 1996.

American Society for Testing Materials (ASTM) Designation: D 5338–92, "Standard Test Method for Determining Aerobic Biodegradation of Plastic Materials Under Controlled Composting Conditions," pp. 456–461, published Feb. 1993.

Good, Robert J. and Robert R. Stromberg, Editors, Surface and Colloid Science—vol. II, Experimental Methods, Plenum Press, New York, 1979, pp. 31–91.

ISO/FDIS 14855:1999(E), "Determination of the ultimate aerobic biodegradability and disintegration of plastic materials under controlled composting conditions—Method by analysis of evolved carbon dioxide," 17 pages.

* cited by examiner

*Primary Examiner*—Kriellion Sanders
(74) *Attorney, Agent, or Firm*—Thomas J. Connelly; John R. Schenian

(57) ABSTRACT

A thermoplastic composition that comprises a unreacted mixture of an aliphatic polyester polymer selected from the group consisting of a polybutylene succinate polymer, a polybutylene succinate-co-adipate polymer, a polycaprolactone polymer, a mixture of such polymers, or a copolymer of such polymers; a multicarboxylic acid; and a wetting agent. The thermoplastic composition is capable of being extruded into fibers that may be formed into nonwoven structures that may be used in a disposable absorbent product intended for the absorption of fluids such as body fluids.

38 Claims, No Drawings

BIODEGRADABLE THERMOPLASTIC COMPOSITION WITH IMPROVED WETTABILITY

BACKGROUND OF THE INVENTION

The present invention relates to a thermoplastic composition that comprises an unreacted mixture of an aliphatic polyester polymer selected from the group consisting of a polybutylene succinate polymer, a polybutylene succinate-co-adipate polymer, a polycaprolactone polymer, a mixture of such polymers, or a copolymer of such polymers; a multicarboxylic acid; and a wetting agent. The thermoplastic composition is capable of being extruded into fibers that may be formed into nonwoven structures that may be used in a disposable absorbent product intended for the absorption of fluids such as body fluids.

DESCRIPTION OF THE RELATED ART

Disposable absorbent products currently find widespread use in many applications. For example, in the infant and child care areas, diapers and training pants have generally replaced reusable cloth absorbent articles. Other typical disposable absorbent products include feminine care products such as sanitary napkins or tampons, adult incontinence products, and health care products such as surgical drapes or wound dressings. A typical disposable absorbent product generally comprises a composite structure including a topsheet, a backsheet, and an absorbent structure between the topsheet and backsheet. These products usually include some type of fastening system for fitting the product onto the wearer.

Disposable absorbent products are typically subjected to one or more liquid insults, such as of water, urine, menses, or blood, during use. As such, the outer cover backsheet materials of the disposable absorbent products are typically made of liquid-insoluble and liquid impermeable materials, such as polypropylene films, that exhibit a sufficient strength and handling capability so that the disposable absorbent product retains its integrity during use by a wearer and does not allow leakage of the liquid insulting the product.

Although current disposable baby diapers and other disposable absorbent products have been generally accepted by the public, these products still have need of improvement in specific areas. For example, many disposable absorbent products can be difficult to dispose of. For example, attempts to flush many disposable absorbent products down a toilet into a sewage system typically lead to blockage of the toilet or pipes connecting the toilet to the sewage system. In particular, the outer cover materials typically used in the disposable absorbent products generally do not disintegrate or disperse when flushed down a toilet so that the disposable absorbent product cannot be disposed of in this way. If the outer cover materials are made very thin in order to reduce the overall bulk of the disposable absorbent product so as to reduce the likelihood of blockage of a toilet or a sewage pipe, then the outer cover material typically will not exhibit sufficient strength to prevent tearing or ripping as the outer cover material is subjected to the stresses of normal use by a wearer.

Furthermore, solid waste disposal is becoming an ever increasing concern throughout the world. As landfills continue to fill up, there has been an increased demand for material source reduction in disposable products, the incorporation of more recyclable and/or degradable components in disposable products, and the design of products that can be disposed of by means other than by incorporation into solid waste disposal facilities such as landfills.

As such, there is a need for new materials that may be used in disposable absorbent products that generally retain their integrity and strength during use, but after such use, the materials may be more efficiently disposed of. For example, the disposable absorbent product may be easily and efficiently disposed of by composting. Alternatively, the disposable absorbent product may be easily and efficiently disposed of to a liquid sewage system wherein the disposable absorbent product is capable of being degraded.

Many of the commercially-available biodegradable polymers are aliphatic polyester materials. Although fibers prepared from aliphatic polyesters are known, problems have been encountered with their use. In particular, aliphatic polyester polymers are known to have a relatively slow crystallization rate as compared to, for example, polyolefin polymers, thereby often resulting in poor processability of the aliphatic polyester polymers. Most aliphatic polyester polymers also have much lower melting temperatures than polyolefins and are difficult to cool sufficiently following thermal processing. Aliphatic polyester polymers are, in general, not inherently wettable materials and may need modifications for use in a personal care application. In addition, the use of processing additives may retard the biodegradation rate of the original material or the processing additives themselves may not be biodegradable.

SUMMARY OF THE INVENTION

The present invention concerns a thermoplastic composition that is desirably biodegradable and yet which is easily prepared and readily processable into desired final structures, such as fibers or nonwoven structures.

One aspect of the present invention concerns a thermoplastic composition that comprises a mixture of a first component, a second component, and a third component.

One embodiment of such a thermoplastic composition comprises a mixture of an aliphatic polyester polymer selected from the group consisting of a polybutylene succinate polymer, a polybutylene succinate-co-adipate polymer, a polycaprolactone polymer, a mixture of such polymers, or a copolymer of such polymers; a multicarboxylic acid, wherein the multicarboxylic acid has a total of carbon atoms that is less than about 30; and a wetting agent which exhibits a hydrophilic-lipophilic balance ratio that is between about 10 to about 40, wherein the thermoplastic composition exhibits desired properties.

In another aspect, the present invention concerns a fiber prepared from the thermoplastic composition wherein the fiber exhibits desired properties.

In another aspect, the present invention concerns a nonwoven structure comprising a fiber prepared from the thermoplastic composition.

One embodiment of such a nonwoven structure is a backsheet useful in a disposable absorbent product.

DETAILED DESCRIPTION OF THE PREFERRED EMBODIMENTS

The present invention is directed to a thermoplastic composition which includes a first component, a second component, and a third component. As used herein, the term "thermoplastic" is meant to refer to a material that softens when exposed to heat and substantially returns to its original condition when cooled to room temperature.

It has been discovered that, by using an unreacted mixture of the components described herein, a thermoplastic composition may be prepared wherein such thermoplastic composition is substantially degradable yet which thermoplastic composition is easily processed into fibers and nonwoven structures that exhibit effective fibrous mechanical properties.

The first component in the thermoplastic composition is an aliphatic polyester polymer selected from the group consisting of a polybutylene succinate polymer, a polybutylene succinate-co-adipate polymer, a polycaprolactone polymer, a mixture of such polymers, or a copolymer of such polymers.

A polybutylene succinate polymer is generally prepared by the condensation polymerization of a glycol and a dicarboxylic acid or an acid anhydride thereof. A polybutylene succinate polymer may either be a linear polymer or a long-chain branched polymer. A long-chain branched polybutylene succinate polymer is generally prepared by using an additional polyfunctional component selected from the group consisting of trifunctional or tetrafunctional polyols, oxycarboxylic acids, and polybasic carboxylic acids. Polybutylene succinate polymers are known in the art and are described, for example, in European Patent Application 0 569 153 A2 to Showa Highpolymer Co., Ltd., Tokyo, Japan.

A polybutylene succinate-co-adipate polymer is generally prepared by the polymerization of at least one alkyl glycol and more than one aliphatic multifunctional acid. Polybutylene succinate-co-adipate polymers are also known in the art.

Examples of polybutylene succinate polymers and polybutylene succinate-co-adipate polymers that are suitable for use in the present invention include a variety of polybutylene succinate polymers and polybutylene succinate-co-adipate polymers that are available from Showa Highpolymer Co., Ltd., Tokyo, Japan, under the designation BIONOLLE™ 1020 polybutylene succinate polymer or BIONOLLE™ 3020 polybutylene succinate-co-adipate polymer, which are essentially linear polymers. These materials are known to be substantially biodegradable.

A polycaprolactone polymer is generally prepared by the polymerization of ε-caprolactone. Examples of polycaprolactone polymers that are suitable for use in the present invention include a variety of polycaprolactone polymers that are available from Union Carbide Corporation, Somerset, N.J., under the designation TONE™ Polymer P767E and TONE™ Polymer P787 polycaprolactone polymers. These materials are known to be substantially biodegradable.

It is generally desired that the aliphatic polyester polymer selected from the group consisting of a polybutylene succinate polymer, a polybutylene succinate-co-adipate polymer, a polycaprolactone polymer, a mixture of such polymers, or a copolymer of such polymers be present in the thermoplastic composition in an amount effective to result in the thermoplastic composition exhibiting desired properties. The aliphatic polyester polymer will be present in the thermoplastic composition in a weight amount that is greater than 0 but less than 100 weight percent, beneficially between about 40 weight percent to less than 100 weight percent, more beneficially between about 50 weight percent to about 95 weight percent, suitably between about 60 weight percent to about 90 weight percent, more suitably between about 60 weight percent to about 80 weight percent, and most suitably between about 70 weight percent to about 75 weight percent, wherein all weight percents are based on the total weight amount of the aliphatic polyester polymer, the multicarboxylic acid, and the wetting agent present in the thermoplastic composition.

It is generally desired that the aliphatic polyester polymer exhibit a weight average molecular weight that is effective for the thermoplastic composition to exhibit desirable melt strength, fiber mechanical strength, and fiber spinning properties. In general, if the weight average molecular weight of an aliphatic polyester polymer is too high, this represents that the polymer chains are heavily entangled which may result in a thermoplastic composition comprising that aliphatic polyester polymer being difficult to process. Conversely, if the weight average molecular weight of an aliphatic polyester polymer is too low, this represents that the polymer chains are not entangled enough which may result in a thermoplastic composition comprising that aliphatic polyester polymer exhibiting a relatively weak melt strength, making high speed processing very difficult. Thus, aliphatic polyester polymers suitable for use in the present invention exhibit weight average molecular weights that are beneficially between about 10,000 to about 2,000,000, more beneficially between about 50,000 to about 400,000, and suitably between about 100,000 to about 300,000. The weight average molecular weight for polymers or polymer blends can be determined by methods known to those skilled in the art.

It is also desired that the aliphatic polyester polymer exhibit a polydispersity index value that is effective for the thermoplastic composition to exhibit desirable melt strength, fiber mechanical strength, and fiber spinning properties. As used herein, "polydispersity index" is meant to represent the value obtained by dividing the weight average molecular weight of a polymer by the number average molecular weight of the polymer. The number average molecular weight for polymers or polymer blends can be determined by methods known to those skilled in the art. In general, if the polydispersity index value of an aliphatic polyester polymer is too high, a thermoplastic composition comprising that aliphatic polyester polymer may be difficult to process due to inconsistent processing properties caused by polymer segments comprising low molecular weight polymers that have lower melt strength properties during spinning. Thus, it is desired that the aliphatic polyester polymer exhibits a polydispersity index value that is beneficially between about 1 to about 15, more beneficially between about 1 to about 4, and suitably between about 1 to about 3.

It is generally desired that the aliphatic polyester polymer be melt processable. It is therefore desired that the aliphatic polyester polymer exhibit a melt flow rate that is beneficially between about 1 gram per 10 minutes to about 200 grams per 10 minutes, suitably between about 10 grams per 10 minutes to about 100 grams per 10 minutes, and more suitably between about 20 grams per 10 minutes to about 40 grams per 10 minutes. The melt flow rate of a material may be determined, for example, according to ASTM Test Method D1238-E, incorporated in its entirety herein by reference.

In the present invention, it is desired that the aliphatic polyester polymer be substantially biodegradable. As a result, the thermoplastic composition comprising the aliphatic polyester polymer, either in the form of a fiber or in the form of a nonwoven structure, will be substantially degradable when disposed of to the environment and exposed to air and/or water. As used herein, "biodegradable" is meant to represent that a material degrades from the action of naturally occurring microorganisms such as bacteria, fungi, and algae. The biodegradability of a material may be determined using ASTM Test Method 5338.92 or ISO CD Test Method 14855, each incorporated in their entirety herein by reference. In one particular embodiment, the biodegradability of a material may be determined using a modified ASTM Test Method 5338.92, wherein the test chambers are maintained at a constant temperature of about 58° C. throughout the testing rather than using an incremental temperature profile.

In the present invention, it is also desired that the aliphatic polyester polymer be substantially compostable. As a result, the thermoplastic composition comprising the aliphatic polyester polymer, either in the form of a fiber or in the form of a nonwoven structure, will be substantially compostable when disposed of to the environment and exposed to air and/or water. As used herein, "compostable" is meant to represent that a material is capable of undergoing biological decomposition in a compost site such that the material is not visually distinguishable and breaks down into carbon dioxide, water, inorganic compounds, and biomass, at a rate consistent with known compostable materials.

The second component in the thermoplastic composition is a multicarboxylic acid. A multicarboxylic acid is any acid that comprises two or more carboxylic acid groups. In one embodiment of the present invention, it is preferred that the multicarboxylic acid be linear. Suitable for use in the present invention are dicarboxylic acids, which comprise two carboxylic acid groups. It is generally desired that the multicarboxylic acid have a total number of carbons that is not too large because then the crystallization kinetics, the speed at which crystallization occurs of a fiber or nonwoven structure prepared from a thermoplastic composition of the present invention, could be slower than is desired. It is therefore desired that the multicarboxylic acid have a total of carbon atoms that is beneficially less than about 30, more beneficially between about 4 to about 30, suitably between about 5 to about 20, and more suitably between about 6 to about 10. Suitable multicarboxylic acids include, but are not limited to, succinic acid, glutaric acid, adipic acid, pimelic acid, suberic acid, azelaic acid, sebacic acid, and mixtures of such acids.

It is generally desired that the multicarboxylic acid be present in the thermoplastic composition in an amount effective to result in the thermoplastic composition exhibiting desired properties. The multicarboxylic acid will be present in the thermoplastic composition in a weight amount that is greater than 0 weight percent, beneficially between greater than 0 weight percent to about 30 weight percent, more beneficially between about 1 weight percent to about 30 weight percent, suitably between about 5 weight percent to about 25 weight percent, more suitably between about 5 weight percent to about 20 weight percent, and most suitably between about 5 weight percent to about 15 weight percent, wherein all weight percents are based on the total weight amount of the aliphatic polyester polymer, the multicarboxylic acid, and the wetting agent present in the thermoplastic composition.

In order for a thermoplastic composition of the present invention to be processed into a product, such as a fiber or a nonwoven structure, that exhibits the properties desired in the present invention, it has been discovered that it is generally desired that the multicarboxylic acid beneficially exists in a liquid state during thermal processing of the thermoplastic composition but that during cooling of the processed thermoplastic composition, the multicarboxylic acid turns into a solid state, or crystallizes, before the aliphatic polyester polymer turns into a solid state, or crystallizes.

In the thermoplastic composition of the present invention, the multicarboxylic acid is believed to perform two important, but distinct, functions. First, when the thermoplastic composition is in a molten state, the multicarboxylic acid is believed to function as a process lubricant or plasticizer that facilitates the processing of the thermoplastic composition while increasing the flexibility and toughness of a final product, such as a fiber or a nonwoven structure, through internal modification of the aliphatic polyester polymer. While not intending to be bound hereby, it is believed that the multicarboxylic acid replaces the secondary valence bonds holding together the aliphatic polyester polymer chains with multicarboxylic acid-to-aliphatic polyester polymer valence bonds, thus facilitating the movement of the polymer chain segments. With this effect, the torque needed to turn an extruder is generally dramatically reduced as compared with the processing of the aliphatic polyester polymer alone. In addition, the process temperature required to spin the thermoplastic composition into a final product, such as a fiber or a nonwoven structure, is generally dramatically reduced, thereby decreasing the risk for thermal degradation of the aliphatic polyester polymer while also reducing the amount and rate of cooling needed for any fiber or nonwoven structure prepared. Second, when a final product prepared from the thermoplastic composition, such as a fiber or a nonwoven structure, is being cooled and solidified from its liquid or molten state, the multicarboxylic acid is believed to function as a nucleating agent. Aliphatic polyester polymers are known to have a very slow crystallization rate. Traditionally, there are two major ways to resolve this issue. One is to change the cooling temperature profile in order to maximize the crystallization kinetics, while the other is to add a nucleating agent to increase the sites and degree of crystallization.

The process of cooling an extruded polymer to ambient temperature is usually achieved by blowing ambient or sub-ambient temperature air over the extruded polymer. Such a process can be referred to as quenching or supercooling because the change in temperature is usually greater than 100° C. and most often greater than 150° C. over a relatively short time frame (seconds). By reducing the melt viscosity of a polymer, such polymer may generally be extruded successfully at lower temperatures. This will generally reduce the temperature change needed upon cooling, to preferably be less than 150° C. and, in some cases, less than 100° C. To customize this common process further into the ideal cooling temperature profile needed to be the sole method of maximizing the crystallization kinetics of aliphatic polyesters in a real manufacturing process is very difficult because of the extreme cooling needed within a very short period of time. Standard cooling methods can be used in combination with a second method of modification, though. The traditional second method is to have a nucleating agent, such as solid particulates, mixed with a thermoplastic composition to provide sites for initiating crystallization during quenching. However, such solid nucleating agents generally agglomerate very easily in the thermoplastic composition which can result in the blocking of filters and spinneret holes during spinning. In addition, the nucleating affect of such solid nucleating agents usually peaks at add-on levels of about 1 percent of such solid nucleating agents. Both of these factors generally reduce the ability or the desire to add in high weight percentages of such solid nucleating agents into the thermoplastic composition. In the processing of the thermoplastic composition of the present invention, however, it has been found that the multicarboxylic acid generally exists in a liquid state during the extrusion process, wherein the multicarboxylic acid functions as a plasticizer, while the multicarboxylic acid is still able to solidify or crystallize before the aliphatic polyester during cooling, wherein the multicarboxylic acid functions as a nucleating agent. It is believed that upon cooling from the homogeneous melt, the multicarboxylic acid solidifies or crystallizes relatively more quickly and completely just as it falls below its melting point since it is a relatively small molecule. For example, adipic acid has a melting temperature of about 162° C. and a crystallization temperature of about 145° C.

The aliphatic polyester polymer, being a macromolecule, has a relatively very slow crystallization rate which means that when cooled it generally solidifies or crystallizes more slowly and at a temperature lower than its melting temperature. During such cooling, then, the multicarboxylic acid starts to crystallize before the aliphatic polyester polymer and generally acts as solid nucleating sites within the cooling thermoplastic composition.

Another major difficulty encountered in the thermal processing of aliphatic polyester polymers into fibers or nonwoven structures is the sticky nature of these polymers. Attempts to draw the fibers, either mechanically, or through an air drawing process, will often result in the aggregation of the fibers into a solid mass. It is generally known that the addition of a solid filler will in most cases act to reduce the tackiness of a polymer melt. However, the use of a solid filler can be problematic in a fiber spinning or nonwoven application were a polymer is extruded through a hole with a very small diameter. This is because the filler particles tend to clog spinneret holes and filter screens, thereby interrupting the fiber spinning process. In the present invention, in contrast, the multicarboxylic acid generally remains a liquid during the extrusion process, but then solidifies almost immediately during the quench process. Thus, the multicarboxylic acid effectively acts as a solid filler, enhancing the overall crystallinity of the system and reducing the tackiness of the fibers and eliminating problems such as fiber aggregation during drawing.

It is desired that the multicarboxylic acid has a high level of chemical compatibility with the aliphatic polyester polymer that the multicarboxylic acid is being mixed with. While the prior art generally demonstrates the feasibility of a polylactide-adipic acid mixture, a unique feature was discovered in this invention. A polylactide-adipic acid mixture can generally only be blended with a relatively minor amount of a wetting agent, such as less than about two weight percent of a wetting agent, and, even then, only with extreme difficulty. Polybutylene succinate, polybutylene succinate-co-adipate, and polycaprolactone have been found to be very compatible with large quantities of both a multicarboxylic acid and a wetting agent. The reason for this is believed to be due to the chemical structure of the aliphatic polyester polymers. Polylactide polymer has a relatively bulky chemical structure, with no linear portions that are longer than $CH_2$. In other words, each $CH_2$ segment is connected to carbons bearing either an oxygen or other side chain. Thus, a multicarboxylic acid, such as adipic acid, can not align itself close to the polylactide polymer backbone. In the case of polybutylene succinate and polybutylene succinate-co-adipate, the polymer backbone has the repeating units $(CH_2)_2$ and $(CH_2)_4$ within its structure. Polycaprolactone has the repeating unit $(CH_2)_5$. These relatively long, open, linear portions that are unhindered by oxygen atoms and bulky side chains align well with a suitable multicarboxylic acid, such as adipic acid, which also has a $(CH_2)_4$ unit, thereby allowing very close contact between the multicarboxylic acid and the suitable aliphatic polyester polymer molecules. This excellent compatibility between the multicarboxylic acid and the aliphatic polyester polymer in these special cases has been found to relatively easily allow for the incorporation of a wetting agent, the third component in the present invention. Such suitable compatibility is evidenced by the ease of compounding and fiber or nonwoven production of mixtures containing polybutylene succinate, polybutylene succinate-co-adipate, polycaprolactone, or a blend or copolymer of these polymers with suitable multicarboxylic acids and wetting agents. The processability of these mixtures is excellent, while in the case of a polylactide-multicarboxylic acid system, a wetting agent can generally not be easily incorporated into the mixture.

Either separately or when mixed together, a polybutylene succinate polymer, a polybutylene succinate-co-adipate polymer, a polycaprolactone polymer, a mixture of such polymers, or a copolymer of such polymers are generally hydrophobic. Since it is desired that the thermoplastic composition of the present invention, and fibers or nonwoven structures prepared from the thermoplastic composition, generally be hydrophilic, it has been found that there is a need for the use of another component in the thermoplastic composition of the present invention in order to achieve the desired properties. As such, the thermoplastic composition of the present invention includes a wetting agent.

Thus, the third component in the thermoplastic composition is a wetting agent for the polybutylene succinate polymer, polybutylene succinate-co-adipate polymer, polycaprolactone polymer, a mixture of such polymers, and/or a copolymer of such polymers. Wetting agents suitable for use in the present invention will generally comprise a hydrophilic section which will generally be compatible with the hydrophilic sections of polybutylene succinate polymer, a polybutylene succinate-co-adipate polymer, a polycaprolactone polymer, a mixture of such polymers, or a copolymer of such polymers and a hydrophobic section which will generally be compatible with the hydrophobic sections of polybutylene succinate polymer, a polybutylene succinate-co-adipate polymer, a polycaprolactone polymer, a mixture of such polymers, or a copolymer of such polymers. These hydrophilic and hydrophobic sections of the wetting agent will generally exist in separate blocks so that the overall wetting agent structure may be di-block or random block. A wetting agent with a melting temperature below, or only slightly above, that of the aliphatic polyester polymer is preferred so that during the quenching process the wetting agent remains liquid after the aliphatic polyester polymer has crystallized. This will generally cause the wetting agent to migrate to the surface of the prepared fibrous structure, thereby improving wetting characteristics and improving processing of the fibrous structure. It is then generally desired that the wetting agent serves as a surfactant in a material processed from the thermoplastic composition, such as a fiber or nonwoven structure, by modifying the contact angle of water in air of the processed material. The hydrophobic portion of the wetting agent may be, but is not limited to, a polyolefin such as polyethylene or polypropylene. The hydrophilic portion of the wetting agent may contain ethylene oxide, ethoxylates, glycols, alcohols or any combinations thereof. Examples of suitable wetting agents include UNITHOX®480 and UNITHOX™750 ethoxylated alcohols, or UNICID™ acid amide ethoxylates, all available from Petrolite Corporation of Tulsa, Okla. Other suitable surfactants can, for example, include one or more of the following:

(1) surfactants composed of silicone glycol copolymers, such as D193 and D1315 silicone glycol copolymers, which are available from Dow Corning Corporation, located in Midland, Mich.

(2) ethoxylated alcohols such as GENAPOL™ 24-L-60, GENAPOL™ 24-L-92, or GENAPOL™ 24-L-98N ethoxylated alcohols, which may be obtained from Hoechst Celanese Corp., of Charlotte, N.C.

(3) surfactants composed of ethoxylated mono- and diglycerides, such as MAZOL™ 80 MGK ethoxylated diglycerides, which is available from PPG Industries, Inc., of Gurnee, Ill.

(4) surfactants composed of carboxylated alcohol ethoxylates, such as SANDOPAN™ DTC, SANDOPAN™ KST, or SANDOPAN™ DTC-100 carboxylated alcohol ethoxylates, which may be obtained from Sandoz Chemical Corp.

(5) ethoxylated fatty esters such as TRYLON™ 5906 and TRYLON™ 5909 ethoxylated fatty esters, which may be obtained from Henkel Corp./Emery Grp. of Cincinnati, Ohio.

It is generally desired that the wetting agent exhibit a weight average molecular weight that is effective for the thermoplastic composition to exhibit desirable melt strength, fiber mechanical strength, and fiber spinning properties. In general, if the weight average molecular weight of a wetting agent is too high, the wetting agent will not blend well with the other components in the thermoplastic composition because the wetting agent's viscosity will be so high that it lacks the mobility needed to blend. Conversely, if the weight average molecular weight of the wetting agent is too low, this represents that the wetting agent will generally not blend well with the other components and have such a low viscosity that it causes processing problems. Thus, wetting agents suitable for use in the present invention exhibit weight average molecular weights that are beneficially between about 1,000 to about 100,000, suitably between about 1,000 to about 50,000, and more suitably between about 1,000 to about 10,000. The weight average molecular weight of 3 wetting agent may be determined using methods known to those skilled in the art.

It is generally desired that the wetting agent exhibit an effective hydrophilic-lipophilic balance ratio (HLB ratio). The HLB ratio of a material describes the relative ratio of the hydrophilicity of the material. The HLB ratio is calculated as the weight average molecular weight of the hydrophilic portion divided by the total weight average molecular weight of the material, which value is then multiplied by 20. If the HLB ratio value is too low, the wetting agent will generally not provide the desired improvement in hydrophilicity. Conversely, if the HLB ratio value is too high, the wetting agent will generally not blend into the thermoplastic composition because of chemical incompatibility and differences in viscosities with the other components. Thus, wetting agents useful in the present invention exhibit HLB ratio values that are beneficially between about 10 to about 40, suitably between about 10 to about 20, and more suitably between about 12 to about 16. The HLB ratio value for a particular wetting agent is generally well known and/or may be obtained from a variety of known technical references.

It is generally desired that the hydrophobic portion of the wetting agent be a linear hydrocarbon chain containing $(CH_2)_n$, where n is preferred to be 4 or greater. This linear hydrocarbon, hydrophobic part is generally highly compatible with similar sections in the polybutylene succinate, polybutylene succinate-co-adipate, and polycaprolactone polymers, as well as many multicarboxylic acids, such as adipic acid. By taking advantage of these structural similarities, the hydrophobic portions of the wetting agent will very closely bind to the aliphatic polyester polymer, while the hydrophilic portions will be allowed to extend out to the surface of a prepared fiber or nonwoven structure. The general consequence of this phenomenon is a relatively large reduction in the advancing contact angle exhibited by the prepared fiber or nonwoven structure. Examples of suitable wetting agents include UNITHOX®480 and UNITHOX®750 ethoxylated alcohols, available from Petrolite Corporation of Tulsa, Okla. These wetting agents have an average linear hydrocarbon chain length between 26 and 50 carbons. If the hydrophobic portion of the wetting agent is too bulky, such as with phenyl rings or bulky side chains, such a wetting agent will generally not be well incorporated into the aliphatic polyester polymer blend. Rather than having the hydrophobic portions of the wetting agent being bound to the aliphatic polyester polymer molecules, with the hydrophilic portions of the wetting agent hanging free, entire molecules of the wetting agent molecules will float freely in the mixture, becoming entrapped in the blend. This is evidenced by a high advancing contact angle and a relatively low receding contact angle, indicating that the hydrophilic chains are not on the surface. After a liquid insult, the wetting agent can migrate to the surface resulting in a low receding contact angle. This is clearly demonstrated through the use of IGEPAL™ RC-630 ethoxylated alkyl phenol surfactant, obtained from Rhone-Poulenc, located in Cranbury, N.J. IGEPAL™ RC-630 ethoxylated alkyl phenol has a bulky phenyl group which limits its compatibility with aliphatic polyester polymers, as evidenced by the high advancing contact angle and low receding contact angle of a mixture of an aliphatic polyester polymer and the IGEPAL™ RC-630 ethoxylated alkyl phenol.

It is generally desired that the wetting agent be present in the thermoplastic composition in an amount effective to result in the thermoplastic composition exhibiting desired properties such as desirable contact angle values. In general, too much of the wetting agent may lead to processing problems of the thermoplastic composition or to a final thermoplastic composition that does not exhibit desired properties such as desired advancing and receding contact angle values. The wetting agent will beneficially be present in the thermoplastic composition in a weight amount that is greater than 0 to about 25 weight percent, more beneficially between about 0.5 weight percent to about 20 weight percent, suitably between about 1 weight percent to about 20 weight percent, and more suitably between about 1 weight percent to about 15 weight percent, wherein all weight percents are based on the total weight amount of the polybutylene succinate polymer, a polybutylene succinate-co-adipate polymer, a polycaprolactone polymer, a mixture of such polymers, or a copolymer of such polymers; the multicarboxylic acid, and the wetting agent present in the thermoplastic composition.

While the principal components of the thermoplastic composition of the present invention have been described in the foregoing, such thermoplastic composition is not limited thereto and can include other components not adversely effecting the desired properties of the thermoplastic composition. Exemplary materials which could be used as additional components would include, without limitation, pigments, antioxidants, stabilizers, surfactants, waxes, flow promoters, solid solvents, plasticizers, nucleating agents, particulates, and other materials added to enhance the processability of the thermoplastic composition. If such additional components are included in a thermoplastic: composition, it is generally desired that such additional components be used in an amount that is beneficially less than about 10 weight percent, more beneficially less than about 5 weight percent, and suitably less than about 1 weight percent, wherein all weight percents are based on the total weight amount of the aliphatic polyester polymer selected from the group consisting of a polybutylene succinate polymer, a polybutylene succinate-co-adipate polymer, a polycaprolactone polymer, a mixture of such polymers, or a copolymer of such polymers; a multicarboxylic acid; and a wetting agent present in the thermoplastic composition.

The thermoplastic composition of the present invention is generally simply a mixture of the aliphatic polyester polymer, the multicarboxylic acid, the wetting agent and, optionally, any additional components. In order to achieve the desired properties for the thermoplastic composition of the present invention, it has been discovered that it is critical that the aliphatic polyester polymer, the multicarboxylic acid, and the wetting agent remain substantially unreacted with each other such that a copolymer comprising each of the aliphatic polyester polymer, the multicarboxylic acid, and/or the wetting agent is not formed. As such, each of the aliphatic polyester polymer, the multicarboxylic acid, and the wetting agent remain distinct components of the thermoplastic composition.

In one embodiment of the present invention, after dry mixing together the aliphatic polyester polymer, the multicarboxylic acid, and the wetting agent to form a thermoplastic composition dry mixture, such thermoplastic composition dry mixture is beneficially agitated, stirred, or otherwise blended to effectively uniformly mix the aliphatic polyester polymer, the multicarboxylic acid, and the wetting agent such that an essentially homogeneous dry mixture is formed. The dry mixture may then be melt blended in, for example, an extruder, to effectively uniformly mix the aliphatic polyester polymer, the multicarboxylic acid, and the wetting agent such that an essentially homogeneous melted mixture is formed. The essentially homogeneous melted mixture may then be cooled and pelletized. Alternatively, the essentially homogeneous melted mixture may be sent directly to a spin pack or other equipment for forming fibers or a nonwoven structure.

Alternative methods of mixing together the components of the present invention include adding the multicarboxylic acid and the wetting agent to the aliphatic polyester polymer in, for example, an extruder being used to mix the components together. In addition, it is also possible to initially melt mix all of the components together at the same time. Other methods of mixing together the components of the present invention are also possible and will be easily recognized by one skilled in the art. In order to determine if the aliphatic polyester polymer, the multicarboxylic acid, and the wetting agent remain essentially unreacted, it is possible to use techniques, such as nuclear magnetic resonance and infrared analysis, to evaluate the chemical characteristics of the final thermoplastic composition.

Typical conditions for thermally processing the various components include using a shear rate that is beneficially between about 100 seconds$^{-1}$ to about 50000 seconds$^{-1}$, more beneficially between about 500 seconds$^{-1}$ to about 5000 seconds$^{-1}$, suitably between about 1000 seconds$^{-1}$ to about 3000 seconds$^{-1}$, and most suitably at about 1000 seconds$^{-1}$. Typical conditions for thermally processing the components also include using a temperature that is beneficially between about 50° C. to about 500° C., more beneficially between about 75° C. to about 300° C., and suitably between about 100° C. to bout 250° C.

As used herein, the term "hydrophobic" refers to a material having a contact angle of water in air of at least 90 degrees. In contrast, as used herein, the term "hydrophilic" refers to a material having a contact angle of water in air of less than 90 degrees. However, commercial personal care products generally require contact angles that are significantly below 90 degrees in order to provide desired liquid transport properties. In order to achieve the rapid intake and wetting properties desired for personal care products, the contact angle of water in air is generally desired to fall below about 70 degrees. In general, the lower the contact angle, the better the wettability. For the purposes of this application, contact angle measurements are determined as set forth in the Test Methods section herein. The general subject of contact angles and the measurement thereof is well known in the art as, for example, in Robert J. Good and Robert J. Stromberg, Ed., in "Surface and Colloid Science—Experimental Methods", Vol. II, (Plenum Press, 1979).

The resultant multicomponent fibers or nonwoven structures of the present invention are desired to exhibit an improvement in hydrophilicity, evidenced by a decrease in the contact angle of water in air. The contact angle of water in air of a fiber sample can be measured as either an advancing or a receding contact angle value because of the nature of the testing procedure. The advancing contact angle measures a material's initial response to a liquid, such as water. The receding contact angle gives a measure of how a material will perform over the duration of a first insult, or exposure to liquid, as well as over following insults. A lower receding contact angle means that the material is becoming more hydrophilic during the liquid exposure and will generally then be able to transport liquids more consistently. Both the advancing and receding contact angle data is desirably used to establish the highly hydrophilic nature of a multicomponent fiber or nonwoven structure of the present invention.

The resultant multicomponent fibers or nonwoven structures of the present invention are desired to exhibit an improvement in the rate of liquid transport, as evidenced by a low contact angle hysteresis. As used herein, the contact angle hysteresis is defined as the difference between the advancing and receding contact angles for a material being evaluated. For example, a relatively high advancing contact angle and relatively low receding contact angle would lead to a large contact angle hysteresis. In such a case, an initial liquid insult would generally be slowly absorbed by a material, though the material would generally retain the liquid once absorbed. In general, relatively low advancing and receding contact angles, as well as a small contact angle hysteresis, are desired in order to have a high rate of liquid transport. Contact angle hysteresis may be used as an indication of the rate of wicking of a liquid on the material being evaluated.

In one embodiment of the present invention, it is desired that a multicomponent fiber or nonwoven structure prepared from the thermoplastic composition described herein exhibits an Advancing Contact Angle value that is beneficially less than about 70 degrees, more beneficially less than about 65 degrees, suitably less than about 60 degrees, more suitably less than about 55 degrees, and most suitably less than about 50 degrees, wherein the Advancing Contact Angle value is determined by the method that is described in the Test Methods section herein.

In another embodiment of the present invention, it is desired that a multicomponent fiber or nonwoven structure prepared from the thermoplastic composition described herein exhibits a Receding Contact Angle value that is beneficially less than about 60 degrees, more beneficially less than about 55 degrees, suitably less than about 50 degrees, more suitably less than about 45 degrees, and most suitably less than about 40 degrees, wherein the Receding Contact Angle value is determined by the method that is described in the Test Methods section herein.

In another embodiment of the present invention, it is desired that a multicomponent fiber or nonwoven structure prepared from the thermoplastic composition described herein exhibits a Advancing Contact Angle value that is beneficially at least about 10 degrees, more beneficially at least about 15 degrees, suitably at least about 20 degrees, and more suitably at least about 25 degrees, less than the Advancing Contact Angle value that is exhibited by an otherwise substantially identical fiber or nonwoven structure prepared from a thermoplastic composition that does not comprise a wetting agent.

In another embodiment of the present invention, it is desired that a multicomponent fiber or nonwoven structure prepared from the thermoplastic composition described herein exhibits a Receding Contact Angle value that is beneficially at least about 5 degrees, more beneficially at least about 10 degrees, suitably at least about 15 degrees, and more suitably at least about 20 degrees, less than the Receding Contact Angle value that is exhibited by an otherwise substantially identical fiber or nonwoven structure prepared from a thermoplastic composition that does not comprise a wetting agent.

As used herein, the term "otherwise substantially identical fiber or nonwoven structure prepared from a thermoplastic composition that does not comprise a wetting agent", and other similar terms, is intended to refer to a control fiber or nonwoven structure that is prepared using substantially identical materials and a substantially identical process as compared to a fiber or nonwoven structure of the present invention, except that the control fiber or nonwoven structure does not comprise or is not prepared with the wetting agent described herein.

In another embodiment of the present invention, it is desired that the difference between the Advancing Contact Angle value and the Receding Contact Angle value, referred to herein as the Contact Angle Hysteresis, be as small as possible. As such, it is desired that the multicomponent fiber exhibits a difference between the Advancing Contact Angle value and the Receding Contact Angle value that is beneficially less than about 50 degrees, more beneficially less than about 40 degrees, suitably less than about 30 degrees, and more suitably less than about 20 degrees.

It is generally desired that the melting or softening temperature of the thermoplastic composition be within a range that is typically encountered in most process applications. As such, it is generally desired that the melting or softening temperature of the thermoplastic composition beneficially be between about 25° C. to about 350° C., more beneficially be between about 35° C. to about 300° C., and suitably be between about 45° C. to about 250° C.

The thermoplastic composition of the present invention has been found to generally exhibit improved processability properties as compared to a thermoplastic composition comprising the aliphatic polyester polymer but none of the multicarboxylic acid and/or the wetting agent. This is generally due to the significant reduction in viscosity that occurs due to the multicarboxylic acid and the internal lubricating effect of the wetting agent. Without the multicarboxylic acid, the viscosity of a mixture of the aliphatic polyester polymer and the wetting agent is generally too high to process. Without the wetting agent, a mixture of the aliphatic polyester polymer and the multicarboxylic acid is generally not a sufficiently hydrophilic material and generally does not have the processing advantages of the liquid wetting agent in the quench zone. It has been discovered as part of the present invention that only with the correct combination of the three components can the appropriate viscosity and melt strength be achieved for fiber spinning.

As used herein, the improved processability of a thermoplastic composition is measured as a decline in the apparent viscosity of the thermoplastic composition at a temperature of about 170° C. and a shear rate of about 1000 seconds$^{-1}$, typical industrial extrusion processing conditions. If the thermoplastic composition exhibits an apparent viscosity that is too high, the thermoplastic composition will generally be very difficult to process. In contrast, if the thermoplastic composition exhibits an apparent viscosity that is too low, the thermoplastic composition will generally result in an extruded fiber that has very poor tensile strength.

Therefore, it is generally desired that the thermoplastic composition exhibits an Apparent Viscosity value at a temperature of about 170° C. and a shear rate of about 1000 seconds$^{-1}$ that is beneficially between about 5 Pascal seconds (Pa.s) to about 200 Pascal seconds, more beneficially between about 10 Pascal seconds to about 150 Pascal seconds, and suitably between about 20 Pascal seconds to about 100 Pascal seconds. The method by which the Apparent Viscosity value is determined is set forth below in connection with the examples.

As used herein, the term "fiber" or "fibrous" is meant to refer to a material wherein the length to diameter ratio of such material is greater than about 10. Conversely, a "nonfiber" or "nonfibrous" material is meant to refer to a material wherein the length to diameter ratio of such material is about 10 or less.

Methods for making fibers are well known and need not be described here in detail. The melt spinning of polymers includes the production of continuous filament, such as spunbond or meltblown, and non-continuous filament, such as staple and short-cut fibers, structures. To form a spunbond or meltblown fiber, generally, a thermoplastic composition is extruded and fed to a distribution system where the thermoplastic composition is introduced into a spinneret plate. The spun fiber is then cooled, solidified, drawn by an aerodynamic system and then formed into a conventional nonwoven. Meanwhile, to produce short-cut or staple the spun fiber is cooled, solidified, and drawn, generally by a mechanical rolls system, to an intermediate filament diameter and collected fiber, rather than being directly formed into a nonwoven structure. Subsequently, the collected fiber may be "cold drawn" at a temperature below its softening temperature, to the desired finished fiber diameter and can be followed by crimping/texturizing and cutting to a desirable fiber length. Fibers can be cut into relatively short lengths, such as staple fibers which generally have lengths in the range of about 25 to about 50 millimeters and short-cut fibers which are even shorter and generally have lengths less than about 18 millimeters.

The thermoplastic composition of the present invention is suited for preparing fibers or nonwoven structures that may be used in disposable products including disposable absorbent products such as diapers, adult incontinent products, and bed pads; in catamenial devices such as sanitary napkins, and tampons; and other absorbent products such as wipes, bibs, wound dressings, and surgical capes or drapes. Accordingly, in another aspect, the present invention relates to a disposable absorbent product comprising the multicomponent fibers of the present invention.

In one embodiment of the present invention, the thermoplastic composition is formed into a fibrous matrix for incorporation into a disposable absorbent product. A fibrous matrix may take the form of, for example, a fibrous nonwoven web. Fibrous nonwoven webs may be made completely from fibers prepared from the thermoplastic composition of the present invention or they may be blended with other fibers. The length of the fibers used may depend on the particular end use contemplated. Where the fibers are to be degraded in water as, for example, in a toilet, it is advantageous if the lengths are maintained at or below about 15 millimeters.

In one embodiment of the present invention, a disposable absorbent product is provided, which disposable absorbent product comprises a liquid-permeable topsheet, a backsheet attached to the liquid-permeable topsheet, and an absorbent structure positioned between the liquid-permeable topsheet and the backsheet, wherein the backsheet comprises fibers prepared from the thermoplastic composition of the present invention.

Exemplary disposable absorbent products are generally described in U.S. Pat. Nos. 4,710,187; 4,762,521; 4,770,656; and U.S. Pat. No. 4,798,603; which references are incorporated herein by reference.

Absorbent products and structures according to all aspects of the present invention are generally subjected, during use, to multiple insults of a body liquid. Accordingly, the absorbent products and structures are desirably capable of absorbing multiple insults of body liquids in quantities to which the absorbent products and structures will be exposed during use. The insults are generally separated from one another by a period of time.

Test Methods
Melting Temperature

The melting temperature of a material was determined using differential scanning calorimetry. A differential scanning calorimeter, available from T.A. Instruments Inc. of New Castle, Del., under the designation Thermal Analyst 2910 Differential Scanning Calorimeter(DSC), which was outfitted with a liquid nitrogen cooling accessory and used in combination with Thermal Analyst 2200 analysis software program, was used for the determination of melting temperatures.

The material samples tested were either in the form of fibers or resin pellets. It is preferred to not to handle the material samples directly, but rather to use tweezers and other tools, so as not to introduce anything that would produce erroneous results. The material samples were cut, in the case of fibers, or placed, in the case of resin pellets, into an aluminum pan and weighed to an accuracy of 0.01 mg on an analytical balance. If needed, a lid was crimped over the material sample onto the pan.

The differential scanning calorimeter was calibrated using an indium metal standard and a baseline correction performed, as described in the manual for the differential scanning calorimeter. A material sample was placed into the test chamber of the differential scanning calorimeter for testing and an empty pan is used as a reference. All testing was run with a 55 cubic centimeter/minute nitrogen (industrial grade) purge on the test chamber. The heating and cooling program is a 2 cycle test that begins with equilibration of the chamber to −20° C., followed by a heating cycle of 20° C./minute to 220° C., followed by a cooling cycle at 20° C./minute to −20° C., and then another heating cycle of 20° C./minute to 220° C.

The results were evaluated using the analysis software program wherein the endothermic and exothermic peaks were identified and quantified.

Apparent Viscosity

A capillary rheometer, under the designation Göttfert Rheograph 2003 capillary rheometer, which was used in combination with WinRHEO (version 2.31) analysis software, both available from Göttfert Company of Rock Hill, S.C., was used to evaluate the apparent viscosity rheological properties of material samples. The capillary rheometer setup included a 2000 bar (200 MPa) pressure transducer and a 30 mm length/30 mm active length/1 mm diameter/0 mm height/180° run in angle, round hole capillary die.

If the material sample being tested demonstrates or is known to have water sensitivity, the material sample is dried in a vacuum oven above its glass transition temperature, i.e. above 55 or 60° C. for poly(lactic acid) materials, under a vacuum of at least 15 inches of mercury (381 mm Hg) with a nitrogen gas purge of at least 30 standard cubic feet per hour (about 0.850 cubic meters per hour) for at least 16 hours.

Once the instrument is warmed up and the pressure transducer is calibrated, the material sample is loaded incrementally into the column, packing the polymer resin pellets into the column with a ramrod each time to ensure a consistent melt during testing. After material sample loading, a 4 minute melt time precedes each test to allow the material sample to completely melt at the test temperature. The capillary rheometer takes data points automatically and determines the apparent viscosity (in Pascal.second) at 7 apparent shear rates (in second$^{-1}$): 50, 100, 200, 500, 1000, 2000, and 5000. When examining the resultant curve it is important that the curve be relatively smooth. If there are significant deviations from a general curve from one point to another, possibly due to air in the column, the test run should be repeated to confirm the results.

The resultant rheology curve of apparent shear rate versus apparent viscosity gives an indication of how the material sample will run at that temperature in an extrusion process. The apparent viscosity values at a temperature of about 170° C. and at a shear rate of about 1000 second$^{-1}$ are of specific interest because these are the typical conditions found in commercial fiber spinning extruders.

Contact Angle

The equipment consists of a DCA-322 Dynamic Contact Angle Analyzer and WinDCA (version 1.02) software, both available from ATI-CAHN Instruments, Inc., of Madison, Wis. Testing was done on the "A" loop with a balance stirrup attached. Calibrations should be done on the balance of the contact angle analyzer with a 100 mg mass before beginning measurements as indicated in the manual. The motor should also be periodically calibrated as per the manual.

Thermoplastic compositions are spun into fibers and the freefall sample (jetstretch of 0) is used for the determination of contact angle. Care should be taken throughout fiber preparation to minimize fiber exposure to handling to ensure that contamination is kept to a minimum. The fiber sample is attached to a wire hanger with scotch tape such that 2–3 cm of fiber extends beyond the end of the hanger. The hanger consists of a 4 cm piece of straight wire that is bent about 0.8 cm from the end so that it forms a hook on that end. Then the fiber sample is cut with a razor so that 1.5 cm extends beyond the end of the hanger. An optical microscope, such as the Leica Galen III, manufactured by Leica, Inc. of Buffalo, N.Y., is used to determine the average diameter (3 to 4 measurements) along the fiber.

The sample on the wire hanger is suspended from the balance stirrup on loop "A" of the contact angle analyzer. The immersion liquid is distilled water and it is changed for each specimen. The specimen parameters are entered (i.e. fiber diameter) and the test started. The stage advances at 151.75 microns/second until it detects the Zero Depth of Immersion when the fiber contacts the surface of the distilled water. From the Zero Depth of Immersion, the fiber advances into the water for 1 cm, dwells for approximately 0 seconds and then immediately recedes 1 cm. The autoanalysis of the contact angle done by the software determines the advancing and receding contact angles of the fiber sample based on standard calculations identified in the manual. Contact angles of 0 or less than 0 indicate that the sample has become totally wettable. Five replicates for each sample are tested and a statistical analysis for mean, standard deviation, and coefficient of variation percent are calculated. As reported in the examples herein and as used throughout the claims, the Advancing Contact Angle value represents the advancing contact angle of distilled water on a fiber sample determined according to the preceding test method. Similarly, as reported in the examples herein and as used throughout the claims, the Receding Contact Angle value represents the receding contact angle of distilled water on a fiber sample determined according to the preceding test method. Contact angle hysteresis is defined as the difference between the advancing and receding contact angles. All values reported herein represent the mean values determined based on the five replicate measurements.

Nonwoven Tensile Testing

Tensile properties of the nonwoven webs were measured on a Sintech 1/D Model, obtained from MTS Systems Corporation, a company located in Eden Prairie Minn., using the Testworks 3.03 analysis software, also obtained from MTS Systems Corporation. A set of 10N pneumatic tensile grips was obtained from MTS (MTS model number 00.01659) and covered with rubber grip facings (MTS model number 38.00401). A 50 lb (about 200 N) load cell is used for this test method, and the rubber-faced, air-actuated grips, are attached to the machine. The power to both the load cell and the load frame is turned on and the equipment given a minimum of one half hour to warm up and stabilize. After this time has elapsed the test grips are moved manually until there is a 3 inch (7.62 cm) separation between the upper and lower grips, as measured with a ruler and a level. The distance is then zeroed on the test software. The grips are opened and the load cell is calibrated.

Samples are cut into one inch (2.54 cm) wide strips which are placed vertically in the grips so that there is no tension on the sample. The test is initiated by the software and the upper grip rises at a rate of 12.0 inches per minute (30.48 cm per minute), while the lower grip remains stationary. The test continues until the nonwoven fails and the upper grip returns to it's starting point. The software then displays the measured and calculated properties of the sample. The information of specific interest is peak and break load, quantities which are directly measured by the machine. Peak load is the maximum load at any point during the test and is measured in grams. Break load is the load, in grams, when the sample fails.

Cup Crush Testing

Cup crush testing was performed on a Sintech 1/D model, obtained from MTS Systems Corporation, a company located in Eden Prairie Minn., using the Testworks 3.03 analysis software, also obtained from MTS Systems Corporation. In this method a 10 lb (about 50 N) load cell is attached to the frame of the Sintech. A forming cylinder is placed on the bottom attachment and a six inch (15.24 cm) by six inch (15.24 cm) nonwoven square is placed over the mouth of the cylinder. The forming cup is placed over the nonwoven, forming the nonwoven over the cylinder, leaving an open circle of the web exposed on top of the cylinder. The foot of the cup crush device consists of a metal rod with a rounded end and is attached to the 10 lb load cell. When the test is initiated the foot descends at a rate of 409.40 mm per minute into the nonwoven web, crushing it. The Sintech then measures the peak load and energy required to crush the nonwoven. The foot descends a total distance of 62 mm and then stops, reverses direction, and returns to its original position. In general a lower peak load indicates a softer nonwoven.

EXAMPLES

Various materials were used as components to form thermoplastic compositions and multicomponent fibers in the following Examples. The designation and various properties of these materials are listed in Table 1.

A poly(lactic acid) (PLA) polymer was obtained from Chronopol Inc., Golden, Colo. under the designation HEPLON™ A10005 poly(lactic acid) polymer. In Table 2, HEPLON™ A10005 poly(lactic acid) polymer is designated as HEPLON.

A polybutylene succinate polymer, available from Showa Highpolymer Co., Ltd., Tokyo, Japan, under the designation BIONOLLE™ 1020 polybutylene succinate, was obtained. In Table 2, BIONOLLE™ 1020 polybutylene succinate polymer is designated as PBS.

A polybutylene succinate-co-adipate, available from Showa Highpolymer Co., Ltd., Tokyo, Japan, under the designation BIONOLLE™ 3020 polybutylene succinate-co-adipate, was obtained. In Table 2, BIONOLLE™ 3020 polybutylene succinate-co-adipate polymer is designated as PBSA.

A polycaprolactone polymer was obtained from Union Carbide Chemicals and Plastics Company, Inc. under the designation TONE™ Polymer P767E polycaprolactone polymer. In Table 2, TONE™ Polymer P767E polycaprolactone polymer is designated as PCL.

A material used as a wetting agent was obtained from Petrolite Corporation of Tulsa, Okla., under the designation UNITHOX™ 480 ethoxylated alcohol, which exhibited a number average molecular weight of about 2250, an ethoxylate percent of about 80 weight percent, a melting temperature of about 65° C., and an HLB value of about 16. In Table 2, UNITHOX™ 480 ethoxylated alcohol is designated as Wetting Agent A.

A material used as a wetting agent was obtained from Baker Petrolite Corporation of Tulsa, Okla., under the designation UNICID™ X-8198 acid amide ethoxylate, which demonstrated an HLB value of approximately 35 and a melting temperature of approximately 60° C. In Table 2, UNICID™ X-8198 acid amide ethoxylate is designated as Wetting Agent B.

A material used as a wetting agent was obtained from Rhone-Poulenc, located in Cranbury, N.J., under the designation IGEPAL™ RC-630 ethoxylated alkyl phenol surfactant, which demonstrated an HLB value of about 12.7 and a melting temperature of about 4° C. In Table 2, IGEPAL™ RC-630 ethoxylated alkyl phenol surfactant is designated as Wetting Agent C.

TABLE 1

| Material Designation | L:D Ratio | Melting Temp. (° C.) | Weight Average Molecular Weight | Number Average Molecular Weight | Poly-dispersity Index | Residual Lactic Acid Monomer |
|---|---|---|---|---|---|---|
| HEPLON A 10005 | 100:0 | 175 | 187,000 | 118,000 | 1.58 | <1% |
| TONE P767E | N/A | 64 | 60,000 | 43,000 | 1.40 | N/A |
| BIONOLLE 1020 | N/A | 95 | 40,000 to 1,000,000 | 20,000 to 300,000 | ≈2 to ≈3.3 | N/A |
| BIONOLLE 3020 | N/A | 114 | 40,000 to 1,000,000 | 20,000 to 300,000 | ≈2 to ≈3.3 | N/A |

Sample Preparation

To prepare a specific thermoplastic composition, the various components were first dry mixed and then melt blended in a counter-rotating twin screw extruder to provide vigorous mixing of the components. The specific materials used in the following examples, and the relative amounts used of each material, are shown in Table 2. The melt mixing involves partial or complete melting of the components combined with the shearing effect of rotating mixing screws. Such conditions are conducive to optimal blending and even dispersion of the components of the thermoplastic composition. Twin screw extruders such as a Haake Rheocord 90 twin screw extruder, available from Haake GmbH of Karlsautte, Germany, or a Brabender twin screw mixer (cat no 05-96-000) available from Brabender Instruments of South Hackensack, N.J., or other comparable twin screw extruders, are well suited to this task. This also includes co-rotating twin screw extruders such as the ZSK-30 extruder, available from Werner and Pfleiderer Corporation of Ramsey, N.J. Unless otherwise indicated, all samples were prepared on a Haake Rheocord 90 twin screw extruder. The melted composition is cooled following extrusion from the melt mixer on either a liquid cooled roll or surface and/or by forced air passed over the extrudate. The cooled composition is then subsequently pelletized for conversion to fibers.

The conversion of these resins into fibers and nonwovens was conducted on an in-house spinning line with a 0.75 inch (1.905 cm) diameter extruder. The extruder has a 24:1 L:D (length:diameter) ratio screw and three heating zones which feed into a transfer pipe from the extruder to the spin pack. The transfer pipe constitutes the 4th and 5th heating zones and contains a 0.62 inch diameter KOCH™ SMX type static mixer unit, available from Koch Engineering Company Inc. of New York, N.Y. The transfer pipe extends into the spinning head (6th heating zone) and through a spin plate with numerous small holes which the molten polymer is extruded through. The temperatures of these heating zones for each composition produced are given in Table 2. The spin plate used herein had 15 holes, where each hole has a 20 mil (0.508 mm) diameter. The fibers are air quenched using air at a temperature of 13° C. to 22° C., drawn down by a mechanical draw roll, and passed on either to a winder unit for collection, or to a fiber drawing unit for spunbond formation and bonding. Alternatively other accessory equipment may be used for treatment before collection. The undrawn, freefall fibers were then evaluated for contact angle and the pelletized resin for melt rheology. The results of this characterization are given in Table 3.

Example 1–7

In these examples, BIONOLLE 1020 polybutylene succinate and BIONOLLE 3020 polybutylene succinate-co-adipate polymers were melt blended in equal weight amounts to provide vigorous mixing of the two components on a ZSK-30 co-rotating twin screw extruder maunfactured by Werner and Pfleiderer. The resulting strands were air cooled and then pelletized. The resultant pellets were dry mixed with adipic acid (product number AD 130 from Spectrum Quality Products, Inc.) and UNITHOX 480 ethoxylated alcohol wetting agent and then melt blended and spun into fibers according to the aforementioned procedure. Three of these examples (Samples 1,3, and 4) were put through a Lurgi process and calendar bonded to form a nonwoven web. Cup crush and tensile tests were performed on these webs and the results are shown in Table 4.

Example 8

In this example, BIONOLLE 1020 polybutylene succinate and BIONOLLE 3020 polybutylene succinate-co-adipate polymers were melt blended in equal weight amounts to provide vigorous mixing of the two components on a ZSK-30 co-rotating twin screw extruder manufactured by Werner and Pfleiderer. The resulting strands were air cooled and then pelletized. The resultant pellets were dry mixed with malonic acid (Aldrich Chemical Company, Milwaukee, Wis., catalog number M129-6) and UNITHOX 480 ethoxylated alcohol wetting agent and then melt blended and fiber spinning was attempted according to the aforementioned method. Attempts at producing fibers were unsuccessful due to severe die swell and dripping of the polymer.

Example 9

In this example, BIONOLLE 1020 polybutylene succinate and BIONOLLE 3020 polybutylene succinate-co-adipate polymers were melt blended in equal weight amounts to provide vigorous mixing of the two components on a ZSK-30 co-rotating twin screw extruder manufactured by Werner and Pfleiderer. The resulting strands were air cooled and then pelletized. The resultant pellets were dry mixed with glutaric acid (Aldrich Chemical Company, Inc., Milwaukee, Wis., catalog number G340-7) and UNITHOX 480 ethoxylated alcohol wetting agent and then melt blended and spun into fibers according to the aforementioned procedure.

Example 10

In this example, BIONOLLE 1020 polybutylene succinate and BIONOLLE 3020 polybutylene succinate-co-adipate polymers were melt blended in equal weight amounts to provide vigorous mixing of the two components on a ZSK-30 co-rotating twin screw extruder manufactured by Werner and Pfleiderer. The resulting strands were air cooled and then pelletized. The resultant pellets were dry mixed with suberic acid (Aldrich Chemical Company, Inc., Milwaukee, Wis., catalog number S520-0) and UNITHOX 480 ethoxylated alcohol wetting agent and then melt blended and spun into fibers according to the aforementioned procedure.

Example 11

In this example, BIONOLLE 1020 polybutylene succinate and BIONOLLE 3020 polybutylene succinate-co-adipate polymers were melt blended in equal weight amounts to provide vigorous mixing of the two components on a ZSK-30 co-rotating twin screw extruder manufactured by Werner and Pfleiderer. The resulting strands were air cooled and then pelletized. The pellets were dry mixed with adipic acid (Spectrum Quality Products, Inc. AD130) and IGEPAL RC-630 ethoxylated alkyl phenol wetting agent and melt blended and spun into fibers as described above.

Example 12

In this example, BIONOLLE 1020 polybutylene succinate and BIONOLLE 3020 polybutylene succinate-co-adipate polymers were melt blended in equal weight amounts to provide vigorous mixing of the two components on a ZSK-30 co-rotating twin screw extruder manufactured by Werner and Pfleiderer. The resulting strands were air cooled and then pelletized. The pellets were dry mixed with adipic acid (Spectrum Quality Products, Inc., product number AD130) and UNICID X-8198 acid amide ethoxylate wetting agent and melt blended and spun into fibers following the previously described method.

Examples 13–20

In these examples, TONE Polymer P767E polycaprolactone polymer was melt blended with adipic acid (Spectrum Quality Products, Inc., product number AD130) and UNITHOX 480 ethoxylated alcohol wetting agent and fiber samples prepared according to the technique described above Example 21

In this example, TONE Polymer P767E polycaprolactone polymer was melt blended with citric acid (Aldrich Chemical Company, Milwaukee, Wis., product number 24,062-1) and UNITHOX 480 ethoxylated alcohol wetting agent and fiber spinning attempted according to the technique described above. Fiber samples were not produced due to foaming and bubbling of the melted resin.

Examples 22–26

In these examples, HEPLON A10005 poly(lactic acid) polymer was melt blended with adipic acid (Spectrum Quality Products, Inc., product number AD130) and UNITHOX 480 ethoxylated alcohol wetting agent and fiber samples prepared according to the aforementioned technique. The compounding of samples 23 and 24 was very difficult due to surging of the extrudate strands and spitting of the wetting agent, due to the incompatibility of polylactide, adipic acid, and the UNITHOX 480 ethoxylated alcohol wetting agent.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

TABLE 2

| Sample No. | Polymer (grams) | | | | Polymer Weight % | Multicarboxylic Acid (grams) | | | | |
| --- | --- | --- | --- | --- | --- | --- | --- | --- | --- | --- |
| | PBS | PBSA | PCL | Heplon | | Adipic Acid | Citric Acid | Malonic Acid | Glutaric Acid | Suberic Acid |
| 1* | 750 | 750 | | | 100 | | | | | |
| 2* | 637.5 | 637.5 | | | 85 | 225 | | | | |
| 3 | 675 | 675 | | | 88.2 | 150 | | | | |
| 4 | 637.5 | 637.5 | | | 83.3 | 225 | | | | |
| 5 | 637.5 | 637.5 | | | 77.3 | 225 | | | | |
| 6 | 637.5 | 637.5 | | | 74.0 | 225 | | | | |
| 7 | 562.5 | 562.5 | | | 74.3 | 375 | | | | |
| 8* | 637.5 | 637.5 | | | 83.3 | | | 225 | | |
| 9 | 637.5 | 637.5 | | | 83.3 | | | | 225 | |
| 10 | 637.5 | 637.5 | | | 83.3 | | | | | 225 |
| 11* | 637.5 | 637.5 | | | 83.3 | 225 | | | | |
| 12* | 637.5 | 637.5 | | | 83.3 | 225 | | | | |
| 13* | | | 1500 | | 100 | | | | | |
| 14* | | | 1125 | | 75.0 | 375 | | | | |
| 15 | | | 1125 | | 74.3 | 375 | | | | |
| 16 | | | 1125 | | 71.4 | 375 | | | | |
| 17 | | | 1125 | | 65.2 | 375 | | | | |
| 18* | | | 750 | | 49.5 | 750 | | | | |
| 19* | | | 1500 | | 99.0 | | | | | |
| 20* | | | 1500 | | 87.0 | | | | | |
| 21* | | | 1125 | | 74.3 | | 375 | | | |
| 22* | | | | 1500 | 100 | | | | | |
| 23* | | | | 1350 | 90.0 | 150 | | | | |
| 24* | | | | 1125 | 75.0 | 375 | | | | |
| 25* | | | | 1125 | 74.3 | 375 | | | | |
| 26* | | | | 1125 | 73.5 | 375 | | | | |

TABLE 2-continued

| Sample No. | Multi-carboxylic Acid Weight % | Wetting Agent (grams) A | B | C | Wetting Agent Weight % | Extrusion Temperature (° C.) | Fiber Spinning Temperatures (° C.) |
|---|---|---|---|---|---|---|---|
| 1* | 0 | | | | 0 | 120/127/123/138 | 180/180/185/190/190/195 |
| 2* | 15 | | | | 0 | 122/127/132/130 | 140/155/155/165/165/165 |
| 3 | 9.8 | 30 | | | 2.0 | 122/127/132/130 | 140/155/155/165/165/165 |
| 4 | 14.7 | 30 | | | 2.0 | 122/127/132/130 | 140/155/155/165/165/165 |
| 5 | 13.6 | 150 | | | 9.1 | 125/127/130/132 | 140/145/145/150/150/150 |
| 6 | 13.0 | 225 | | | 13.0 | 125/127/130/132 | 140/145/145/150/150/150 |
| 7 | 24.7 | 15 | | | 1.0 | 125/127/130/132 | 130/130/135/135/140/143 |
| 8* | 14.7 | 30 | | | 2.0 | 125/130/132/135 | would not process |
| 9 | 14.7 | 30 | | | 2.0 | 125/130/135/135 | 135/140/140/145/150/150 |
| 10 | 14.7 | 30 | | | 2.0 | 125/130/135/135 | 140/140/150/150/155/155 |
| 11* | 14.7 | | | 30 | 2.0 | 125/127/130/132 | 140/145/145/150/150/150 |
| 12* | 14.7 | | 30 | | 2.0 | 125/127/130/132 | 140/145/145/150/150/150 |
| 13* | 0 | | | | 0 | None used | 190/190/195/195/200/205 |
| 14* | 25.0 | | | | 0 | 135/137/145/147 | 145/150/150/155/155/155 |
| 15 | 24.7 | 15 | | | 1.0 | 115/120/122/110 | 140/140/145/145/145/150 |
| 16 | 23.8 | 75 | | | 4.8 | 120/126/126/118 | 120/125/130/130/130/135 |
| 17 | 21.7 | 225 | | | 13.1 | 60/70/70/80 | 120/120/120/125/125/130 |
| 18* | 49.5 | 15 | | | 1.0 | 120/125/125/122 | 130/130/135/135/140/140 |
| 19* | 0 | 15 | | | 1.0 | 60/62/64/70 | 160/160/160/165/170/175 |
| 20* | 0 | 225 | | | 13.0 | 60/62/64/70 | 160/160/160/165/170/175 |
| 21* | 24.7 | 15 | | | 1.0 | 90/100/100/90 | would not process |
| 22* | 0 | | | | 0 | None used | 160/180/190/190/190/190 |
| 23* | 10.0 | | | | 0 | 155/155/165/165 | 155/155/160/160/160/165 |
| 24* | 25.0 | | | | 0 | 155/175/185/185 | 150/170/165/160/160/160 |
| 25* | 24.7 | 15 | | | 1.0 | 165/170/170/150 | 150/150/155/160/160/165 |
| 26* | 24.5 | 30 | | | 2.0 | 165/167/167/145 | 150/150/155/160/160/165 |

*Not an example of the present invention

TABLE 3

| Sample # | Advancing Contact Angle | Receding Contact Angle | Contact Angle Hysteresis | Shear Viscosity @1000s$^{-1}$, 170° C. (Pa.s) |
|---|---|---|---|---|
| 1* | 97 | 70 | 27 | 203 |
| 2* | 83 | 24 | 59 | 56 |
| 3 | 58 | 27 | 31 | 61 |
| 4 | 53 | 27 | 26 | 50 |
| 5 | 60 | 41 | 19 | 18 |
| 6 | 52 | 41 | 11 | 11 |
| 7 | 68 | 16 | 52 | 24 |
| 8* | N/A | N/A | N/A | N/A |
| 9 | 62 | 15 | 47 | 13 |
| 10 | 56 | 19 | 37 | 24 |
| 11* | 93 | 38 | 56 | 40 |
| 12* | 80 | 55 | 25 | 34 |
| 13* | 86 | 61 | 25 | 243 |
| 14* | 81 | 54 | 27 | 54 |
| 15 | 62 | 36 | 26 | 45 |
| 16 | 62 | 35 | 27 | 24 |
| 17 | 49 | 33 | 16 | 11 |
| 18* | 72 | 40 | 32 | 9 |
| 19* | 49 | 41 | 8 | 257 |
| 20* | 54 | 40 | 14 | 179 |
| 21* | N/A | N/A | N/A | N/A |
| 22* | 87 | 55 | 32 | N/A |
| 23* | 75 | 55 | 20 | 23 |
| 24* | 85 | 56 | 29 | 12 |
| 25* | 79 | 45 | 34 | 24 |
| 26* | 76 | 38 | 38 | 15 |

*Not an example of the present invention

TABLE 4

| | Cup Crush Properties | | | |
|---|---|---|---|---|
| | Tensile Properties | | Total Energy | Peak Load |
| Sample # | Peak Load (g) | Break Load (g) | (g · mm) | (g) |
| 1 | 168 | 153 | 66 | 6 |
| 3 | 414 | 402 | 199 | 13 |
| 4 | 856 | 837 | 248 | 17 |

What is claimed is:

1. A thermoplastic composition comprising a mixture of:
   a. an aliphatic polyester polymer selected from the group consisting of a polybutylene succinate polymer, a polybutylene succinate-co-adipate polymer, a polycaprolactone polymer, a mixture of such polymers, or a copolymer of such polymers, wherein the aliphatic polyester polymer exhibits a weight average molecular weight that is between about 10,000 to about 2,000,000, wherein the aliphatic polyester polymer is present in the thermoplastic composition in a weight amount that is between about 40 to less than 100 weight percent;
   b. a multicarboxylic acid having a total of carbon atoms that is less than about 30, wherein the multicarboxylic acid is present in the thermoplastic composition in a weight amount that is between greater than 0 weight percent to about 30 weight percent; and
   c. a wetting agent, which exhibits a hydrophilic-lipophilic balance ratio that is between about 10 to about 40, in a weight amount that is greater than 0 to about 25 weight percent, wherein all weight percents are based on the total weight amount of the aliphatic polyester polymer, the multicarboxylic acid, and the wetting agent present in the thermoplastic composition;
   wherein the thermoplastic composition exhibits an Apparent Viscosity value at a temperature of about 170° C. and a shear rate of about 1000 seconds$^{-1}$ that is between about 5 Pascal seconds and about 200 Pascal seconds.

2. The thermoplastic composition of claim 1 wherein the aliphatic polyester polymer is a polybutylene succinate polymer.

3. The thermoplastic composition of claim 1 wherein the aliphatic polyester polymer is a polybutylene succinate-co-adipate polymer.

4. The thermoplastic composition of claim 1 wherein the aliphatic polyester polymer is a polycaprolactone polymer.

5. The thermoplastic composition of claim 1 wherein the aliphatic polyester polymer is present in the thermoplastic composition in a weight amount that is between about 50 weight percent to about 95 weight percent.

6. The thermoplastic composition of claim 5 wherein the aliphatic polyester polymer is present in the thermoplastic composition in a weight amount that is between about 60 weight percent to about 90 weight percent.

7. The thermoplastic composition of claim 1 wherein the multicarboxylic acid is selected from the group consisting of succinic acid, glutaric acid, adipic acid, pimelic acid, suberic acid, azelaic acid, sebacic acid, and a mixture of such acids.

8. The thermoplastic composition of claim 7 wherein the multicarboxylic acid is selected from the group consisting of glutaric acid, adipic acid, and suberic acid.

9. The thermoplastic composition of claim 1 wherein the multicarboxylic acid is present in the thermoplastic composition in a weight amount that is between about 1 weight percent to about 30 weight percent.

10. The thermoplastic composition of claim 9 wherein the multicarboxylic acid is present in the thermoplastic composition in a weight amount that is between about 5 weight percent to about 25 weight percent.

11. The thermoplastic composition of claim 1 wherein the multicarboxylic acid has a total of carbon atoms that is between about 4 to about 30.

12. The thermoplastic composition of claim 1 wherein the wetting agent exhibits a hydrophilic-lipophilic balance ratio that is between about 10 to about 20.

13. The thermoplastic composition of claim 1 wherein the wetting agent is present in the thermoplastic composition in a weight amount that is between about 0.5 weight percent to about 20 weight percent.

14. The thermoplastic composition of claim 1 wherein the wetting agent is present in the thermoplastic composition in a weight amount that is between about 1 weight percent to about 15 weight percent.

15. The thermoplastic composition of claim 1 wherein the wetting agent is selected from the group consisting of ethoxylated alcohols, acid amide ethoxylates, and ethoxylated alkyl phenols.

16. The thermoplastic composition of claim 1 wherein the aliphatic polyester polymer is present in the thermoplastic composition in a weight amount that is between about 50 weight percent to about 95 weight percent, the multicarboxylic acid is selected from the group consisting of succinic acid, glutaric acid, adipic acid, pimelic acid, suberic acid, azelaic acid, sebacic acid, and a mixture of such acids and is present in the thermoplastic composition in a weight amount that is between about 1 weight percent to about 30 weight percent, and the wetting agent is selected from the group consisting of ethoxylated alcohols, acid amide ethoxylates, and ethoxylated alkyl phenols and is present in the thermoplastic composition in a weight amount that is between about 0.5 weight percent to about 20 weight percent.

17. A fiber prepared from a thermoplastic composition, the thermoplastic composition comprising a mixture of:
   a. an aliphatic polyester polymer selected from the group consisting of a polybutylene succinate polymer, a polybutylene succinate-co-adipate polymer, a polycaprolactone polymer, a mixture of such polymers, or a copolymer of such polymers, wherein the aliphatic polyester polymer exhibits a weight average molecular weight that is between about 10,000 to about 2,000,000, wherein the aliphatic polyester polymer is present in the thermoplastic composition in a weight amount that is between about 40 to less than 100 weight percent;
   b. a multicarboxylic acid having a total of carbon atoms that is less than about 30, wherein the multicarboxylic acid is present in the thermoplastic composition in a weight amount that is between greater than 0 weight percent to about 30 weight percent; and
   c. a wetting agent, which exhibits a hydrophilic-lipophilic balance ratio that is between about 10 to about 40, in a weight amount that is greater than 0 to about 25 weight percent, wherein all weight percents are based on the total weight amount of the aliphatic polyester polymer, the multicarboxylic acid, and the wetting agent present in the thermoplastic composition;
wherein the fiber exhibits an Advancing Contact Angle value that is less than about 70 degrees and a Receding Contact Angle value that is less than about 60 degrees.

18. The fiber of claim 17 wherein the aliphatic polyester polymer is present in the thermoplastic composition in a weight amount that is between about 50 weight percent to about 95 weight percent.

19. The fiber of claim 18 wherein the aliphatic polyester polymer is present in the thermoplastic composition in a weight amount that is between about 60 weight percent to about 90 weight percent.

20. The fiber of claim 17 wherein the multicarboxylic acid is selected from the group consisting of succinic acid, glutaric acid, adipic acid, pimelic acid, suberic acid, azelaic acid, sebacic acid, and a mixture of such acids.

21. The fiber of claim 20 wherein the multicarboxylic acid is selected from the group consisting of glutaric acid, adipic acid, and suberic acid.

22. The fiber of claim 17 wherein the multicarboxylic acid is present in the thermoplastic composition in a weight amount that is between about 1 weight percent to about 30 weight percent.

23. The fiber of claim 22 wherein the multicarboxylic acid is present in the thermoplastic composition in a weight amount that is between about 5 weight percent to about 25 weight percent.

24. The fiber of claim 17 wherein the multicarboxylic acid has a total of carbon atoms that is between about 4 to about 30.

25. The fiber of claim 17 wherein the wetting agent exhibits a hydrophilic-lipophilic balance ratio that is between about 10 to about 20.

26. The fiber of claim 17 wherein the wetting agent is present in the thermoplastic composition in a weight amount that is between about 0.5 weight percent to about 20 weight percent.

27. The fiber of claim 26 wherein the wetting agent is present in the thermoplastic composition in a weight amount that is between about 1 weight percent to about 15 weight percent.

28. The fiber of claim 17 wherein the wetting agent is selected from the group consisting of ethoxylated alcohols, acid amide ethoxylates, and ethoxylated alkyl phenols.

29. The fiber of claim 17 wherein the fiber exhibits an Advancing Contact Angle value that is less than about 65 degrees.

30. The fiber of claim 17 wherein the fiber exhibits a Receding Contact Angle value that is less than about 55 degrees.

31. The fiber of claim 17 wherein the fiber exhibits a Receding Contact Angle value that is less than about 50 degrees.

32. The fiber of claim 17 wherein the aliphatic polyester polymer is present in the thermoplastic composition in a weight amount that is between about 50 weight percent to about 95 weight percent, the multicarboxylic acid is selected from the group consisting of succinic acid, glutaric acid, adipic acid, pimelic acid, suberic acid, azelaic acid, sebacic acid, and a mixture of such acids and is present in the thermoplastic composition in a weight amount that is between about 1 weight percent to about 30 weight percent, and the wetting agent is selected from the group consisting of ethoxylated alcohols, acid amide ethoxylates, and ethoxylated alkyl phenols and is present in the thermoplastic composition in a weight amount that is between about 0.5 weight percent to about 20 weight percent.

33. The fiber of claim 17 wherein the aliphatic polyester polymer is polybutylene succinate polymer, the multicarboxylic acid is adipic acid, and the wetting agent is an ethoxylated alcohol.

34. The fiber of claim 17 wherein the aliphatic polyester polymer is polybutylene succinate-co-adipate polymer, the multicarboxylic acid is adipic acid, and the wetting agent is an ethoxylated alcohol.

35. The fiber of claim 17 wherein the aliphatic polyester polymer is a mixture of polybutylene succinate polymer and polybutylene succinate-co-adipate polymer, the multicarboxylic acid is adipic acid, and the wetting agent is an ethoxylated alcohol.

36. The fiber of claim 17 wherein the aliphatic polyester polymer is a mixture of polybutylene succinate polymer and polybutylene succinate-co-adipate polymer, the multicarboxylic acid is glutaric acid, and the wetting agent is an ethoxylated alcohol.

37. The fiber of claim 17 wherein the aliphatic polyester polymer is a mixture of polybutylene succinate polymer and polybutylene succinate-co-adipate polymer, the multicarboxylic acid is suberic acid, and the wetting agent is an ethoxylated alcohol.

38. The fiber of claim 17 wherein the aliphatic polyester polymer is polycaprolactone polymer, the multicarboxylic acid is adipic acid, and the wetting agent is an ethoxylated alcohol.

* * * * *

UNITED STATES PATENT AND TRADEMARK OFFICE
CERTIFICATE OF CORRECTION

PATENT NO. : 6,225,388 B1
DATED : May 1, 2001
INVENTOR(S) : Fu-Jya Tsai, Brigitte Wertheim Page 1 of 1

It is certified that error appears in the above-identified patent and that said Letters Patent is hereby corrected as shown below:

<u>Title page,</u>
Item [57], ABSTRACT,
Line 1, delete "a" and substitute -- an --.

<u>Column 7,</u>
Line 26, delete "were" and substitute -- where --.

<u>Column 9,</u>
Line 36, delete "3" and substitute -- a --.

<u>Column 11,</u>
Line 65, delete "bout" and substitute -- about --.

<u>Column 13,</u>
Line 8, delete "a" and substitute -- an --.

<u>Column 17,</u>
Line 51, delete "it's" and substitute -- its --.

Signed and Sealed this

Twelfth Day of March, 2002

*Attest:*

JAMES E. ROGAN
*Attesting Officer*     *Director of the United States Patent and Trademark Office*